United States Patent [19]

Brouwer

[11] Patent Number: 4,956,855
[45] Date of Patent: Sep. 11, 1990

[54] X-RAY LINE DETECTOR DEVICE AND X-RAY ANALYSIS APPARATUS COMPRISING SUCH A DEVICE

[75] Inventor: Geert Brouwer, Waalre, Netherlands

[73] Assignee: U.S. Philips Corporation, New York, N.Y.

[21] Appl. No.: 252,952

[22] Filed: Oct. 3, 1988

[30] Foreign Application Priority Data

Oct. 16, 1987 [NL] Netherlands .................. 8702474

[51] Int. Cl.⁵ ............................................. G01N 23/223
[52] U.S. Cl. ........................................ 378/45; 378/49; 378/44; 250/370.01

[58] Field of Search .................. 378/19, 44–46, 378/49, 70–71, 84–85; 250/338.4, 370.01, 370.04, 370.10

[56] References Cited

U.S. PATENT DOCUMENTS 4,800,580  1/1989  Houtman et al. ...................... 378/71

Primary Examiner—Craig E. Church
Assistant Examiner—John C. Freeman
Attorney, Agent, or Firm—Paul R. Miller

[57] ABSTRACT

An X-ray line detector where signals from detector elements are selectively combined in dependence on the deflection angle of the X-ray beam from the X-ray source and an object carrier.

4 Claims, 1 Drawing Sheet

X-RAY LINE DETECTOR DEVICE AND X-RAY ANALYSIS APPARATUS COMPRISING SUCH A DEVICE

The invention relates to an X-ray line detector device comprising an array of parallel arranged solid state detector elements.

An X-ray line detector device of this kind is known from Netherlands Patent Application 8 300 419. FIG. 4c of the cited publication shows an X-ray line detector of the kind set forth in which the width of each solid-state detector element is constant, but differs from one element to another. Furthermore, the solid state detector elements are selectively interconnected in two groups in order to enable the elimination of background current and dark current and the detection of peak shifts.

It is the object of the present invention to provide an X-ray line detector device which enables the detection of not only straight X-ray lines but also of curved X-ray lines with optimum intensity and optimum resolution.

To achieve this, an X-ray line detector device of the kind set forth in accordance with the invention is characterized in that each of the solid state detector elements has the same width and is identically segmented into a number of neighbouring, separate segments, the central portion of a central segment having a width which approximates that of the solid state detector element, its end portions having a substantially smaller width, the width of the end portions of the other segments being substantially larger than that of their central portion.

The invention also provides an X-ray analysis apparatus comprising an X-ray source, an object carrier, an X-ray line detector device and a signal processing device connected to the X-ray line detector device.

The X-ray analysis apparatus of the kind set forth is also known from the cited publication.

In order to achieve the same object as before, the X-ray analysis apparatus of the kind set forth in accordance with the invention is characterized in that the X-ray line detector device is a device in accordance with the invention, the signal processing device selectively combining the signals from neighbouring segments of the X-ray line detector device in dependence of the deflection angle of the X-ray beam from the X-ray source to the object carrier.

Like in the cited publication, the X-ray analysis apparatus may be embodied in a spectrometer or a diffractometer in which the X-ray lines are spectral lines and diffraction lines, respectively.

The invention will be described in detail hereinafter with reference to the drawing; therein:

Figure 1:
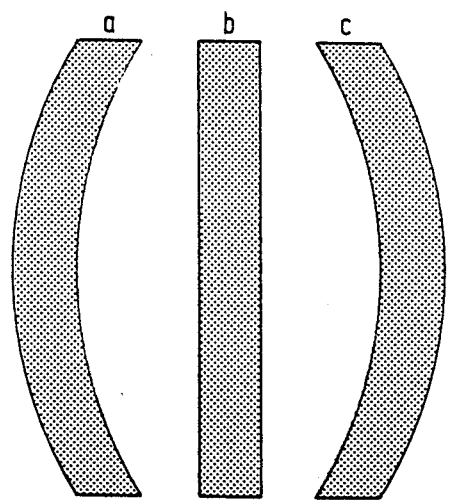
FIG. 1 shows a number of feasible X-ray lines.

When curved focusing optical systems are used, X-ray lines are produced which may be curved in different directions in dependence of the deflection angle $\theta$ of the X-ray beam emitted by the X-ray source (not shown) to an object carrier (not shown). FIG. 1 shows three types of X-ray lines, that is to say a, b and c from left to right, where $\theta$ is larger than, equal to and smaller than $\pi/4$, respectively.

Figure 2:
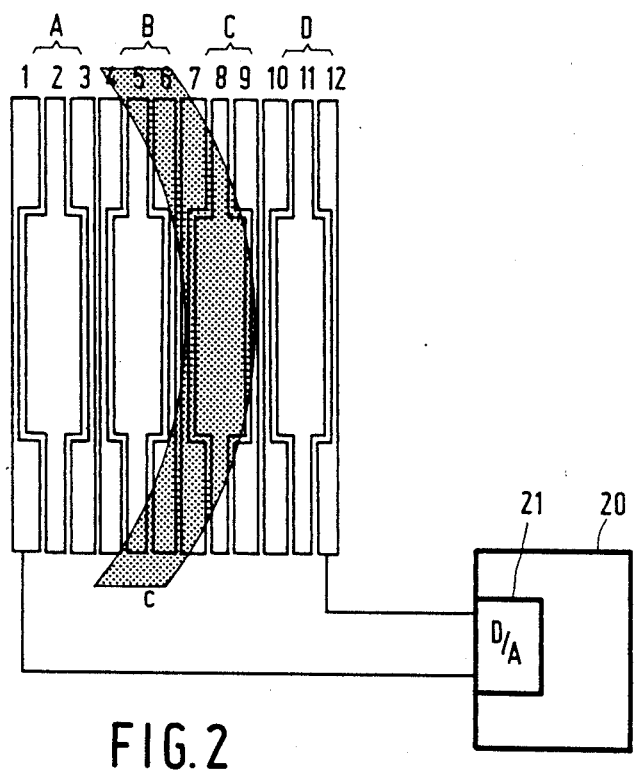
FIG. 2 shows a part of the X-ray line detector device in accordance with the invention and (in very simplified form) a part of the X-ray analysis device, reference being made to the cited publication for a description of the other constituent parts.

The X-ray line c is also shown in FIG. 2. FIG. 2 also shows a part of an array of parallel arranged, equally long solid state detector elements A-D which are formed, for example by silicon diodes. The solid state elements A-D in this case have the same width and are identically segmented into a number of neighbouring separate segments 1-3, 4-6, 7-9 and 10-12, respectively, a central segment of which, in this case 2, 5, 8 and 11, respectively, has a central portion whose width approximates that of the solid state detector elements A-D, respectively, and whose end portions have a substantially smaller width. The other segments, i.e. 1 and 3, 4 and 6, 7 and 9 and 10 and 12, respectively, have end portions having a width which is substantially larger than that of their central portion. As appears from FIG. 2, the end portions of all segments can have at least approximately the same width.

An X-ray line of the type c can thus be measured with optimum resolution and optimum intensity by connecting the segments 6, 7 and 8 in parallel or by combining the signals originating therefrom, for example by addition. For an X-ray line of the type b, the segments 7, 8 and 9 can be combined; for the type a the segments 8, 9 and 10 can be combined.

The X-ray line profile is usually not as abrupt as depicted herein and a rather Gaussian function distribution exists. When an X-ray line of, for example the type c is recorded, in that case not only the segments 6, 7 and 8 will be combined, but also 3, 4 and 5 and 9, 10 and 11. It is not always necessary to combine time three segments 1-12.

FIG. 2 also shows a signal processing device 20 which preferably comprises a digital-to-analog converter 21 for digitizing the signals originating from the segments 1-12, followed by suitable selective combination. When a spectrum or a diffractogram is scanned, for example the signal processing device 20 can ensure that the relevant signals of the segments 1-12 are combined by taking into account the phase differences of the successive measurements. Furthermore, the combination of the signals from the segments 1-12 can be rendered dependent of the deflection angle $\theta$, so that a continuous change-over takes place from the type a to the type c.

What is claimed is:

1. An X-ray line detector device, comprising an array of parallel arranged solid state detector elements, characterized in that each of the solid state detector elements has the same width and is identically segmented into a plurality of neighboring separate segments, comprising a central segment and an adjacent segment wherein a central portion of said central segment having a width which approximates that of the solid state detector element, said central segment further comprising end portions having a substantially smaller width than the central portion of said central segment, and wherein said adjacent segment comprises a central portion and end portions, wherein the width of the end portions of said adjacent segment is substantially larger than the width of the central portion of said adjacent segment.

2. An X-ray line detector device as claimed in claim 1, characterized in that the end portions of said central and adjacent segments have at least approximately the same width.

3. An X-ray line detector device as in claim 1 or 2 further comprising an X-ray analysis apparatus including an X-ray source, an object carrier, and a signal processing device connected to the array of solid state detector elements wherein the signal processing device selectively combines the signals from neighbouring segments of the array of solid state detector elements in dependence of the deflection angle of the X-ray beam from the X-ray source to the object carrier.

4. An X-ray analysis apparatus as claimed in claim 3, characterized in that the signal processing device comprises an analog-to-digital converter for digitizing the signals from neighboring segments prior to combination.

* * * * *